United States Patent [19]

Dafforn et al.

[11] Patent Number: 4,981,786

[45] Date of Patent: Jan. 1, 1991

[54] MULTIPLE PORT ASSAY DEVICE

[75] Inventors: Geoffrey A. Dafforn, Los Altos; Nurith Kurn; Martin Becker, both of Palo Alto; Edwin F. Ullman, Atherton, all of Calif.

[73] Assignee: Syntex (U.S.A.) Inc., Palo Alto, Calif.

[21] Appl. No.: 94,176

[22] Filed: Sep. 4, 1987

[51] Int. Cl.5 .................. G01N 33/535; G01N 21/01
[52] U.S. Cl. ............................. 435/7; 422/56;
422/58; 422/101; 422/102; 436/514; 436/541;
436/810; 435/805; 435/810
[58] Field of Search .............. 436/514, 541, 810;
422/55–58, 101, 102; 435/7, 805, 810

[56] References Cited

U.S. PATENT DOCUMENTS

| 4,233,029 | 11/1980 | Columbus | 422/55 |
| 4,254,083 | 3/1981 | Columbus | 422/55 |
| 4,693,834 | 9/1987 | Hossom | 422/101 |
| 4,738,823 | 4/1988 | Engelmann | 422/56 |
| 4,818,677 | 4/1989 | Hay-Kaufman et al. | 422/56 |
| 4,847,199 | 7/1989 | Snyder et al. | 422/101 |

*Primary Examiner*—Christine Nucker
*Attorney, Agent, or Firm*—Theodore J. Leitereg

[57] ABSTRACT

A device is disclosed for conducting an assay. The device comprises a housing, means enclosed in the housing for capturing a first member of a specific binding pair (sbp) in a zone and for allowing liquid to be transported by capillary action away from the zone, first means in the housing for introducing the sample into the device, and second means in the housing other than the first means for introducing a liquid reagent other than the sample into the device. The device of the invention finds use in assay methods for the determination of an analyte in a sample suspected of containing the analyte. Kits for conducting an assay are also disclosed.

52 Claims, 5 Drawing Sheets

MULTIPLE PORT ASSAY DEVICE

BACKGROUND OF THE INVENTION

1. Field of the Invention

This invention relates to devices for conducting assays. The ability to employ receptors directed to specific compounds in assaying for the presence of a compound of interest has created a burgeoning diagnostic assay business. Over the years, numerous simplified test systems have been developed for the rapid detection of materials of interest in biological and industrial fluids. These systems or devices in their simplest form usually involve the combination of a test reagent specifically reactable with the material of interest to give a visual response and a bibulous carrier for the test reagent. Paper is the most commonly used material for the carrier. A portion of the carrier is usually impregnated or coated with one or more of the test reagents. The portion of the carrier containing the test reagents is brought into contact with the sample containing the material of interest. The contact may be accomplished by immersing the portion of the carrier with the test reagents into the sample in an aqueous medium or an aqueous sample can be allowed to traverse a bibulous carrier by capillary migration through the portion of the carrier containing the test reagent. The test zone may be first created on the carrier or the zone may be produced during the running of the assay.

A concentrating zone method in heterogeneous assays has found broad application. The method employs a device that has an immunosorbing zone to which a specific binding pair member is fixed non-diffusively. The immunosorbing zone serves as an entry for the sample and reagent solutions. In liquid receiving relationship, either directly or indirectly with the immunosorbing zone, is a liquid absorbing zone which serves to draw liquid through the immunosorbing zone, store liquid and may serve to control the rate at which the liquid is drawn through the immunosorbing zone. Employed in the method in conjunction with the device is a signal producing system which has a signal label member conjugated to a specific binding pair member. The immunosorbing zone may include one or more members of the signal producing system which are bound to the zone in a manner to permit or inhibit diffusive movement of the signal producing system component. In accordance with the method protocol, the amount of signal label bound in the detection zone in the immunosorbing zone is related to the amount of the material of interest in the sample. In the method the assay device is contacted with liquid sample to which may have been added one or more components of the signal producing system. The device may subsequently be contacted with one ore more solutions which contain remaining components of the signal producing system and serve to wash the immunosorbing zone free of non-specifically bound signal label. The signal producing system provides for a detectible signal in the immunosorbing zone which can be compared to a signal level based on a standard having a known amount of analyte.

The concentrating zone method technology has been applied in a number of commercial products, such as, for example, the ICON ® device (Hybritech Corporation), the TESTPACK TM device (Abbott Laboratories), and the SUDS TM device (Murex Corporation). One problem with the known devices is that the sample solution and wash and reagent solutions are generally added through the same entry port and portions of the device that are wet by these solutions immediately contaminate subsequently added wash or reagent solutions.

A capillary transport technique for carrying out qualitative and/or quantitative assays for an analyte are also known. The assay involves contacting a portion of a bibulous material with a liquid medium containing the analyte and optionally other members of a signal producing system, which includes a labeled specific binding pair member. The bibulous material usually contains one or more zones for specifically binding the analyte. The bibulous material may also have on its surface one or more members of a signal producing system. The liquid medium is allowed to traverse the bibulous material by capillary action and the bibulous material is contacted with remaining members of the signal producing system. The presence of analyte in a sample can be determined by examining the bibulous material for a signal at the appropriate zone and the quantity of analyte can be determined by relating the position of a border between signal and no signal in a zone to the amount of analyte in the sample or counting the number of zones having or not having a signal and relating the number of zones to the amount of analyte in the sample. Exemplary of a capillary transport technique in accordance with the first approach above is a capillary immunochromatography product sold by Syva Company under the name Acculevel TM.

It is desirable to provide an immunoassay device having broad application to heterogeneous assays. The device should be simple, rapid, accurate, and safe for unskilled persons to perform in environments outside of sophisticated laboratory settings. It is also desirable to provide a diagnostic device for conducting such assays wherein contamination of various reagents during their addition to the device used in the assay is avoided. Such a device would be convenient and efficient.

2. Description of the Related Art

A concentrating zone method in heterogeneous immunoassays is described in U.S. Pat. No. 4,366,241. A test device for detecting low concentrations of substances in fluids is described in U.S. Pat. No. 3,811,840. An improved heterogeneous immunoassay method and assembly is discussed in European Application Publication No. 0 141 547. U.S. Pat. No. 4,517,288 discloses a solid phase system for ligand assay. An integrated material for chemical analysis and a method of using the same is discussed in U.S. Pat. No. 4,270,920. The performance of routine chemical reactions in compartmentalized containers is described in U.S. Pat. No. 3,825,410. An immunodiffusion plate apparatus is described in U.S. Pat. No. 3,645,687. The performance of chemical or biological reactions within an absorbent matrix pad is discussed in U.S. Pat. No. 3,888,629. A test device for assaying liquid samples for the presence of a predetermined reagent is described in U.S. Pat. No. 4,246,339. An immobilized antibody or antigen for immunoassay is disclosed in U.S. Pat. No. 4,407,943. U.S. Pat. No. 3,915,647 discloses a device for determining the concentration of a substance in a fluid. U.S. Pat. No. 4,632,901 describes a method and apparatus for immuno-assays. PCT application WO 86/06488 describes a diagnostic device having a plurality of rupturable containers.

SUMMARY OF THE INVENTION

The invention described herein is a device for conducting an assay. The device comprises a housing, means enclosed in the housing for capturing a first member of a specific binding pair (sbp) in a zone and for allowing liquid to be transported by capillary action away from the zone. The reagents are those utilized in conducting an assay for the determination of an analyte in a sample. The housing is also provided with first means for introducing a sample into the device and second means other than the first means for introducing a liquid reagent other than the sample into the device without also introducing said liquid reagent through said first means. The device of the invention finds use in assay methods for the determination of an analyte in a sample suspected of containing the analyte. The invention further includes kits for conducting an assay. The device of the present invention is a compact system devised for convenient on site testing of a variety of analytes.

DESCRIPTION OF THE SPECIFIC EMBODIMENTS

One aspect of the present invention concerns a device for conducting an assay. The device comprises a housing and means enclosed in the housing for capturing a first member of a specific binding pair (sbp) in a zone and for allowing liquid to be transported by capillary action away from the zone. The housing further includes first means for introducing the sample into the device and second means for introducing a liquid reagent other than the sample into the device that permits the liquid reagent to enter the device without it entering through the first means. The device of the invention finds use in assay methods for the determination of an analyte in a sample suspecting of containing the analyte. One or more self-contained reagents may also be enclosed in the housing for conducting an assay method for the determination of an analyte in the sample.

The device of the present invention has broad application. The device may be utilized in any number of assays wherein absorbent material is utilized to assist the flow of liquid away from a contact portion where the absorbent material is contacted with a medium containing the analyte to be determined or reagents for analyzing for the analyte. The device of the present invention is simple to use, normally requiring merely introducing the sample and other reagents in liquid form into the device through the first means and the second means as appropriate. The device can also include additional means other than the first means and the second means for introducing additional assay reagents into the device.

Before proceeding further with the description of the specific embodiments of the present invention, a number of terms will be defined.

Analyte—the compound or composition to be measured that is capable of binding specifically to a ligand or receptor, usually an antibody or antigen such as a protein or drug; a member of a specific binding pair.

The precise nature of antigenic and drug analytes together with numerous examples thereof are disclosed in U.S. Pat. No. 4,299,916 to Litman, et al., particularly columns 16 to 23, and in U.S. Pat. No. 4,275,149, columns 17 and 18, the disclosures of which are incorporated herein by reference.

The analytes are characterized by having single binding sites (monovalent) or multiple binding sites (polyvalent). The polyvalent analytes will normally be poly(amino acids), i.e., polypeptides and proteins, polysaccharides, nucleic acids, and combinations thereof. Such combinations or assemblages include bacteria, viruses, chromosomes, genes, mitochondria, nuclei, cell membranes, and the like.

A wide variety of proteins may be considered as to the family of proteins having similar structural features, proteins having particular biological functions, particularly antibodies, proteins related to specific microorganisms, particularly disease causing microorganisms, etc. Exemplary of microbiological analytes are lipsopolysaccharides, proteins and nucleic acids from organisms such as chlamydia, herpes virus, hepatitis virus (A, B, or non-A-non-B), gonorrhea, T. pallidum, and the like.

The following are classes of proteins related by structure: protamines, histones, albumins, globulins, scleroproteins, phosphoproteins, mucoproteins, chromoproteins, lipoproteins, nucleoproteins, glycoproteins, proteoglycans, unclassified proteins, e.g. somatotorophin, prolactin, insulin, pepsin.

A number of proteins found in human plasma are important clinically and include: prealbumin, albumin, $\alpha_1$-lipoprotein, $\alpha_1$-acid glycoprotein, $\alpha_1$-antitrypsin, $\alpha_1$-glycoprotein, transcortin, 4.6S-postalbumin, tryptophan-poor $\alpha_1$-glycoprotein, $\alpha_1\chi$-glycoprotein, thyroxin-binding globulin, inter-$\alpha$-trypsin-inhibitor, Gc-globulin, haptoglobulin, ceruloplasmin, cholinesterase, $\alpha_2$-lipoprotein(s), myoglobin, C-reactive Protein, $\alpha_2$-macroglobulin, $\alpha_2$HS-glycoprotein, Zn-$\alpha_2$-glycoprotein, $\alpha_2$-neuramino-glycoprotein, erythropoietin, $\beta$-lipoprotein, transferrin, hemopexin, fibrinogen, plasminogen, $\beta_2$-glycoprotein I, $\beta_2$-glycoprotein II and specific binding proteins such as antibodies to microbial antigens, autoimmune antibodies, T cell receptors, antibodies to allergens, particularly IgE, and the like.

Complement factors and blood clotting factors are exemplary of analytes. Important protein hormones such as Parathyroid hormone, Thyrocalcitonin, Insulin, Glucagon, Relaxin, Erythropoietin, Melanotropin, Somatotropin, Corticotropin, Thyrotropin, Follicle-stimulating hormone, Luteinizing hormone, Luteomammotropic hormone, Gonadotropin (chorionic gonadotropin);

Tissue Hormones such as secretin, gastrin, angiotensin I and II, bradykinin, human placental lactogen are exemplary of analytes.

Peptide Hormones from the Neurohypophysis such as oxytocin, vasopressin, releasing factors (RF) CRF, LRF, TRF, somatotropin-RF, GRF, FSH-RF, PIF, MIF are exemplary of analytes.

The monoepitopic ligand analytes will generally by from about 100 to 2,000 molecular weight, more usually from 125 to 1,000 molecular weight. The analytes of interest include drugs, metabolites, pesticides,. pollutants, and the like. Included among drugs of interest are the alkaloids. Among the alkaloids are morphine alkaloids, which includes morphine, codeine, heroin, dextromethorphan their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular or ring members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narcine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g., $B_{12}$, C, D, E and K, folic acid, and thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, AND, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2\times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

Member of a specific binding pair ("sbp member") —one of two different molecules having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormone-hormone receptor, nucleic acid duplexes, IgG-protein A, DNA-DNA, DNA-RNA, and the like are not immunological pairs but are included in the definition.

Ligand—any organic compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq. and the like.

Labeled sbp member—a label, generally capable of electrochemical detection or absorption or emission of electromagnetic radiation, a catalyst, frequently an enzyme, bound to a first sbp member. The labeled sbp member is a member of the signal producing system and the first sbp member is chosen to bind to the second sbp member in accordance with a particular protocol in an assay.

Antibody—an immunoglobulin, or derivative or fragment thereof, having an area on the surface or in a cavity which specifically binds to and is thereby defined as complementary with a particular spatial and polar organization of another molecule. The antibody can be monoclonal or polyclonal and can be prepared by techniques, that are well known in the art such as, for example, immunization of a host and collection of sera or hybrid cell line technology.

Antibody for the analyte—an antibody specific for an analyte.

Bibulous material—a porous material having pores of at least 0.1μ, preferably at least 1.0μ, which is susceptible to traversal by an aqueous medium in response to capillary force. Such materials are generally hydrophilic or are capable of being rendered hydrophilic and include inorganic powders such as silica, magnesium sulfate, and alumina; natural polymeric materials, particularly cellulosic materials and materials derived from cellulose, such as fiber containing papers, e.g., filter paper, chromatographic paper, etc.; glass fibers; synthetic or modified naturally occurring polymers, such as nitrocellulose, cellulose acetate, poly (vinyl chloride), polyacrylamide, cross linked dextran, agarose, polyacrylate, etc.; either used by themselves or in conjunction with other materials; ceramic materials; and the like. The bibulous material can be attached to a support. On the other hand, the bibulous material may provide its own support. The bibulous material may be polyfunctional or be capable of being polyfunctionalized to permit covalent bonding of receptors or antibodies as well as to permit bonding of other compounds which form a part of the signal producing system.

Binding of receptors and antibodies to the bibulous material may be accomplished by well-known techniques, commonly available in the literature. See, for example, "Immobilized Enzymes," Ichiro Chibata, Halsted Press, New York (1978) and Cuatrecasas, *J. Bio. Chem.*, 245:3059 (1970).

The piece of bibulous material can be a single structure such as a sheet cut into strips or it can be several strips or particulate material bound to a support or solid surface such as found, for example, in thin-layer chromatography and may have an absorbent pad either as an integral part or in liquid contact. The piece of bibulous material can also be a sheet having lanes thereon, capable of spotting to induce lane formation, wherein a separate assay can be conducted in each lane. The piece of bibulous material can have a rectangular, circular, oval, triagonal or other shape provided that there is at least one direction of traversal of a test solution by capillary migration. Other directions of traversal may occur such as in an oval or circular piece contacted in the center with the test solution. However, the main consideration is that there be at least one direction of flow to a predetermined site. In the following discussion strips of bibulous material will be described by way of illustration and not limitation.

The support for the bibulous material, where a support is desired or necessary, will normally be water insoluble, frequently non-porous and rigid but may be elastic, usually hydrophobic, and porous and usually will be of the same length and width as the bibulous strip but may be larger or smaller. A wide variety of organic and inorganic materials, both natural and synthetic, and combinations thereof, may be employed provided only that the support does not interfere with the capillary action of the bibulous materials, or non-specifically bind assay components, or interfere with the signal producing system. Illustrative polymers include polyethylene, polypropylene, poly(4-methylbutene), polystyrene, polymethacrylate, poly(ethylene terephthalate), nylon, poly(vinyl butyrate), glass, ceramics, metals, and the like. Elastic supports may be made of polyurethane, neoprene, latex, silicone rubber and the like.

Label—A label may be any molecule bound to an sbp member that is required to produce a signal. In the subject invention, the label may be inert and serve solely as a binding site for a member of the signal producing system or it may spontaneously produce a detectable signal or may produce a detectable signal in conjunction with a signal producing system. The label may be isotopic or nonisotopic, preferably nonisotopic. However, an isotopic label can be preferred for achieving high sensitivity when using radio-autographic detections with photographic film.

Signal producing means—means capable of interacting with the label to produce a detectible signal. Such means include, for example, electromagnetic radiation, heat, chemical reagents, and the like. Where chemical reagents are employed, some of the chemical reagents can be included as part of a developer solution. The chemical reagents can include substrates, coenzymes, enhancers, second enzymes, activators, cofactors, inhibitors, scavengers, metal ions, specific binding substances required for binding of signal generating substances, and the like. Some of the chemical reagents such as coenzymes, substances that react with enzymic products, other enzymes and catalysts, and the like can be bound to the bibulous material.

Signal producing system—The signal producing system may have one or more components, at least one component usually being a labeled sbp member. The signal producing system includes all of the reagents required to produce a measurable signal including signal producing means capable of interacting with a label to produce a signal.

The signal producing provides a signal detectable by external means, normally by measurement of electromagnetic radiation, desirably by visual examination. For the most part, the signal producing system includes a chromophoric substrate and enzyme, where chromophoric substrates are enzymatically converted to dyes which absorb light in the ultraviolet or visible region, phosphors or fluorescers.

The signal producing system can include at least one catalyst as a label, usually at least one enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal at the predetermined site, related to the presence of label at the predetermined site.

Two catalysts may be employed, either a combination of an enzyme and a non-enzyme catalyst or two enzymes, where the two catalysts are related in that the product of one is the substrate of the other. In this system, there need be only one substrate which can undergo successive changes catalyzed by the catalysts, which results in the compound involved with production of a detectable signal. For the most part, however, there will normally be a substrate for the first enzyme in the series and a second compound, which serves as a precursor to the compound involved in the production of the signal, normally providing the compound which produces the signal. Thus, the product of the first enzyme may react with the precursor to the compound that produces a signal to provide the compounds that generates the signal.

Where the two enzymes are employed, the involved reactions will be, for the most part, hydrolysis or redox reactions. In the case of hydrolysis, a derivatized dye precursor that haS a hydrolytically labile bond, the hydrolytic enzyme and an enzyme that catalyzes the released dye precursors to a dye conversion product is illustrative of this type of system. In redox reactions, a first enzyme can produce an essential oxidizing substrate required for the second enzyme, where the second enzyme catalyzes the reaction between the oxidizing substrate and a dye precursor.

Where two enzymes are used, the first enzymatic reaction may involve hydrolytic cleavage or a redox reaction of the substrate to provide a product which is the substrate of another enzyme. The first situation may be illustrated by glucose-6-phosphate being catalytically hydrolyzed by alkaline phosphatase to glucose, where glucose is a substrate for glucose oxidase. The second situation may be illustrated by glucose being oxidized by glucose oxidase to provide hydrogen peroxide which would enzymatically react with a leuco dye to produce a signal generator.

Coupled catalysts can also involve an enzyme with a non-enzymatic catalyst. The enzyme can produce a reactant which undergoes a reaction catalyzed by the non-enzymatic catalyst or the non-enzymatic catalyst may produce a substrate (includes coenzymes) for the enzyme. A wide variety of non-enzymatic catalysts which may be employed are found in U.S. Pat. No. 4,160,645, issued July 10, 1979, the appropriate portions of which are incorporated herein by reference.

Various combinations of enzymes may be employed to provide a signal generating compound. Particularly, combinations of hydrolases may be employed to produce an insoluble signal generator. Alternatively, combinations of hydrolases and oxidoreductases can provide the signal generating compound. Also, combinations of oxidoreductases may be used to produce an insoluble signal generating compound.

For combinations of enzymes one enzyme can be non-diffusively bound to the bibulous material, while the other enzyme is the label conjugated to the analyte. Additionally, one or more other members of the signal producing system can be bound to the bibulous material depending on the particular signal producing system chosen or the particular protocol followed.

In order to have a detectable signal, it is desirable to provide means for amplifying the signal produced by the presence of the label at the predetermined site. Therefore, it will usually be preferable for the label to be a catalyst or luminescent compound or radioisotope, most preferably a catalyst. Preferably, catalysts are enzymes and coenzymes which can produce a multiplicity of signal generating molecules from a single label.

An enzyme or coenzyme is employed which provides the desired amplification by producing a product, which absorbs light, e.g., a dye, or emits light upon irradiation, e.g., a fluorescer. Alternatively, the catalytic reaction can lead to direct light emission, e.g., chemiluminescence. A large number of enzymes and coenzymes for providing such products are indicated in U.S. Pat. No. 4,275,149 bridging columns 19 to 23, and U.S. Pat. No. 4,318,980, columns 10 to 14, which disclosures are incorporated herein by reference.

A number of enzyme combinations are set forth in U.S. Pat. No. 4,275,149, bridging columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably, hydrolases such as alkaline phosphatase and $\beta$-galactosidase. Alternatively luciferases may be used such as firefly luciferase and bacterial luciferase.

Illustrative coenzymes which find use include AND[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

Ancillary materials—Various ancillary materials will frequently be employed in the assay in accordance with the present invention. For example, buffers will normally be present in the assay medium, as well as stabilizers. Frequently, in addition to these additives, additional proteins may be included, such as albumins, or surfactants, particularly, non-ionic surfactants, binding enhancers, e.g. polyalkylene glycols, or the like.

Immunoconcentrating assembly—the immunoconcentrating assembly generally has an immunosorbing zone and a liquid absorbing zone. The immunosorbing zone and the liquid absorbing zone are usually engaged in a liquid receiving relationship either directly or indirectly. The immunoconcentrating assembly can include one or more immunosorbing zones. The immunosorbing zone and the liquid absorbing zone can form one integral unit such as a strip having one or more immunosorbing zones. Alternatively, the immunosorbing zone and the liquid absorbing zone can be distinct. For example, the immunosorbing zone may be a membrane to which an sbp member is attached. The liquid absorbing zone can be absorbent material in the form of a strip, pad, plug, wick, or the like, in liquid receiving relationship with the immunosorbing zone. The liquid absorbent material can be of any hydrophilic bibulous material such as paper, sponge, felt, porous polymers and the like.

Immunosorbing zone—a bibulous solid film, layer or sheet, frequently in contact with or a portion of the piece of bibulous material, to which a sbp member, usually an antibody or antigen, is non-diffusively bound. Immunosorbing zone frequently has a small fluid capacity as compared to the total assay device capacity. One or more members of a signal producing system may be bound directly or indirectly to the immunosorbing zone. The immunosorbing zone has a specific binding capability for a complementary sbp member.

Liquid absorbing zone—a bibulous solid material either directly or indirectly in liquid receiving relationship with the immunosorbing zone and acting as a reservoir or storage zone capable of a storing a substantially greater liquid volume than the immunosorbing zone. The liquid absorbing zone acts as a pump to pump liquid through and out of the immunosorbing zone. The liquid absorbing zone serves to control the volume of the fluid that traverses the immunosorbing zone. A further function for the liquid absorbing zone may be to measure the amount of liquid which is passed through the device. By providing for graduations at sequential positions extending away from the immunosorbing zone and along the liquid absorbing zone, one can determine when the solvent front is at a certain position. One can provide for dyes which will become colored upon dissolution or contact with a solvent front to provide an indication that the solvent has traversed the device.

Liquid reagent(s)—one or more liquid reagents for conducting an assay employing the device of the invention. The liquid reagent can include a sbp member, members of a signal producing system, or suspension of particles bound to a sbp member or member of a signal producing system, ancillary reagents, or the like and will usually be aqueous.

Self-contained liquid reagent—described in U.S. Ser. No. 035,562, filed Apr. 7, 1987, the disclosure of which is incorporated herein by reference. The liquid reagent can be confined in at least one breakable container in the device of the invention. The container can be integral with the housing of the present device or separate therefrom or both where more than one self-contained reagent is employed. Upon breaking the container(s) the reagent is rendered capable of traversing the bibulous material employed in the present assay device.

The device of the present invention will next be described in more detail with reference to the attached drawings. It should be emphasized that the following description is by way of illustration and not limitation. Various specific embodiments of the present invention will be suggested to those skilled in the art with the present description in mind. Such embodiments are intended to be within the scope of the present invention.

Figures 1, 1A:
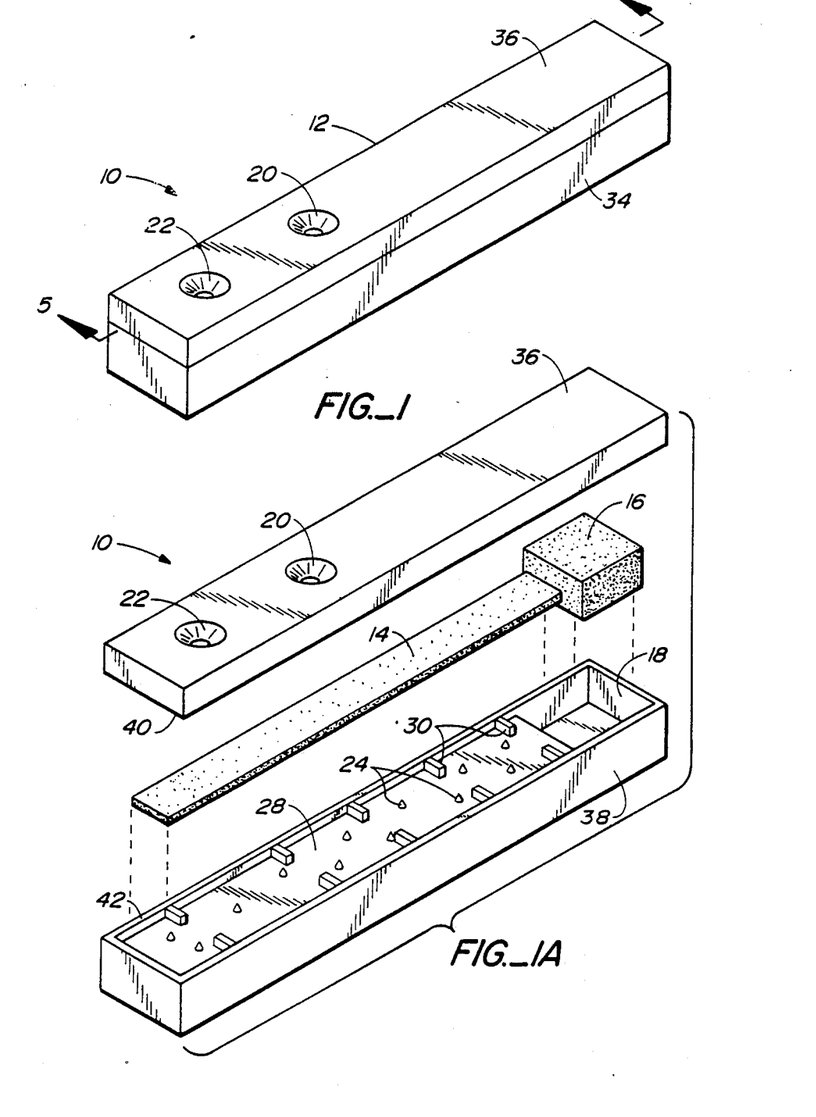
FIG. 1 is a top perspective view taken slightly from the side of a device in accordance with the present invention.
FIG. 1A is an exploded view of the device of FIG. 1.
Figure 2:
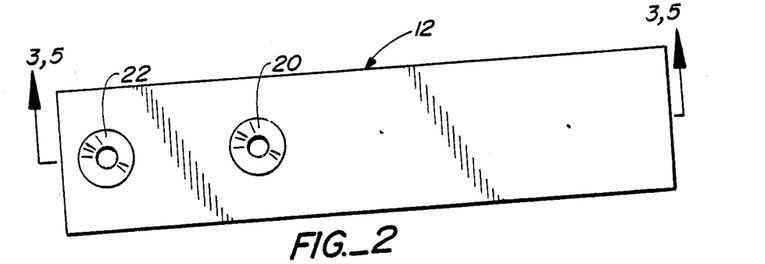
FIG. 2 is a top plan view of the device of FIG. 1.
Figure 3:
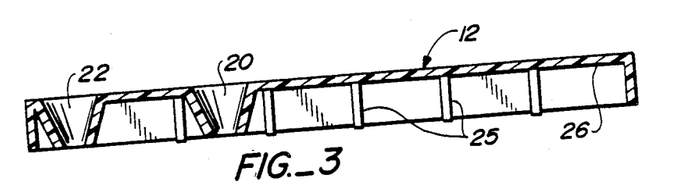
FIG. 3 is a cross-sectional view of the top half of the device of FIG. 1 taken along lines 3—3.
Figure 4:
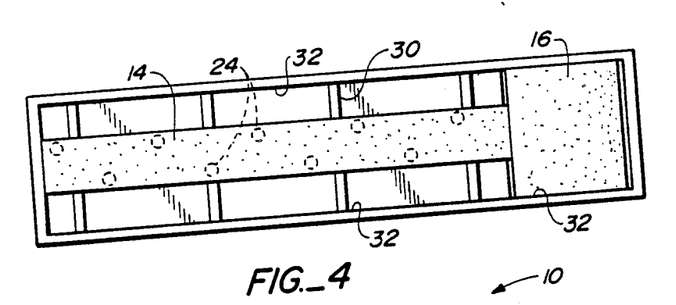
FIG. 4 is a top view of the bottom half of the device of FIG. 1.
Figure 5:
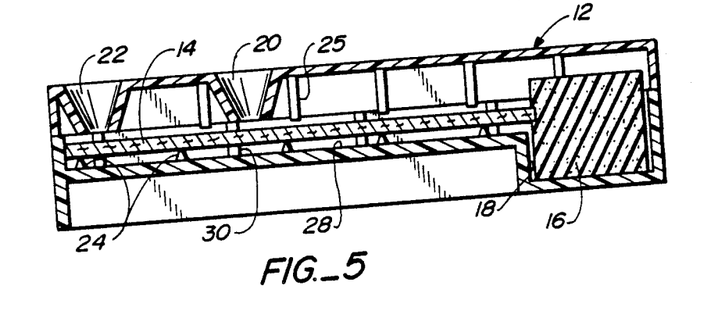
FIG. 5 is a cross-sectional view of the device of FIG. 1 taken along lines 5—5.
Figure 6:
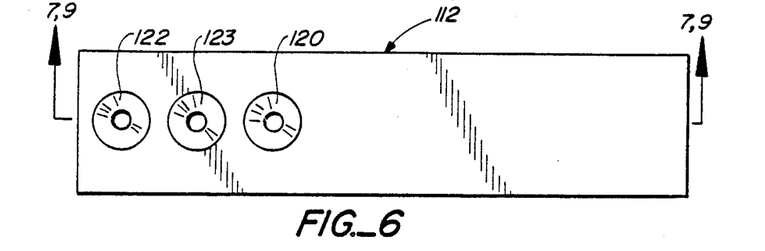
FIG. 6 is a top plan view the side of another embodiment of the device of the present invention.
Figure 7:
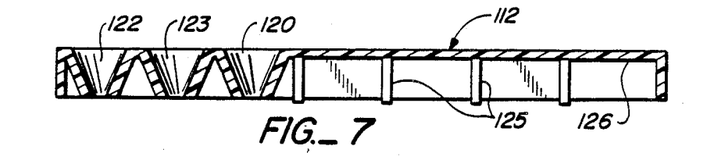
FIG. 7 is a cross-sectional view of the top of the device of FIG. 6 taken along lines 7—7.
Figure 8:
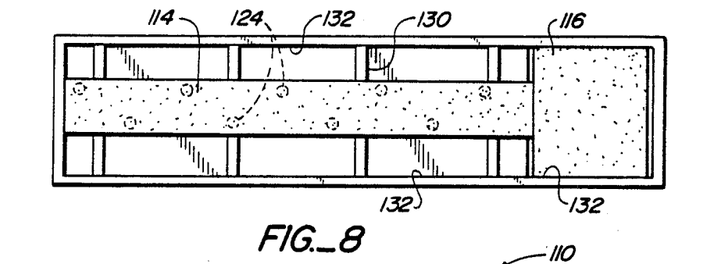
FIG. 8 is a top view of the bottom half of the device of FIG. 5.
Figure 9:
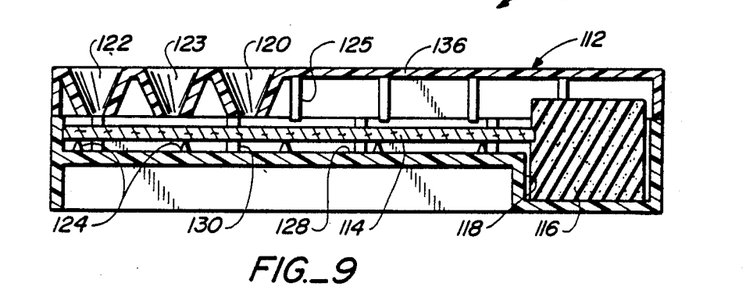
FIG. 9 is a cross-sectional view of the device of FIG. 5 taken along lines 9—9.
Figure 10:
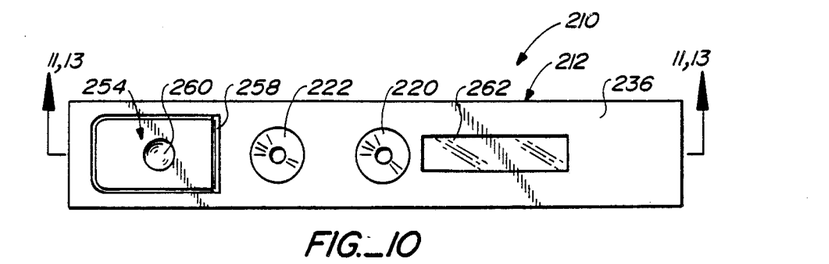
FIG. 10 is a top plan view of another embodiment of the device of the present invention.
Figure 11:
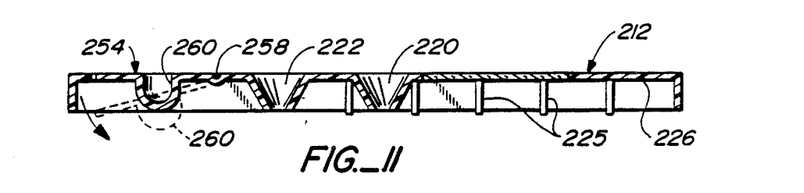
FIG. 11 is a cross-sectional view of the top half of the device of FIG. 10 taken along lines 11—11.
Figure 12:
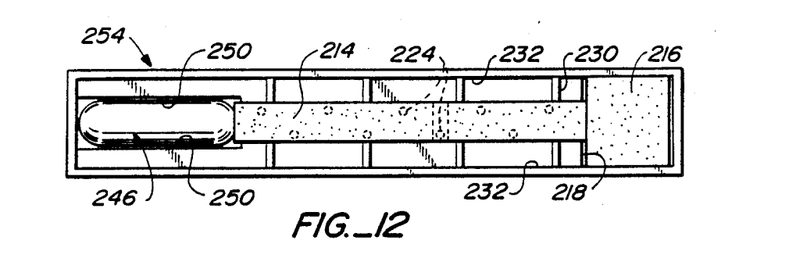
FIG. 12 is a top view of the bottom half of the device of FIG. 10.
Figure 13:
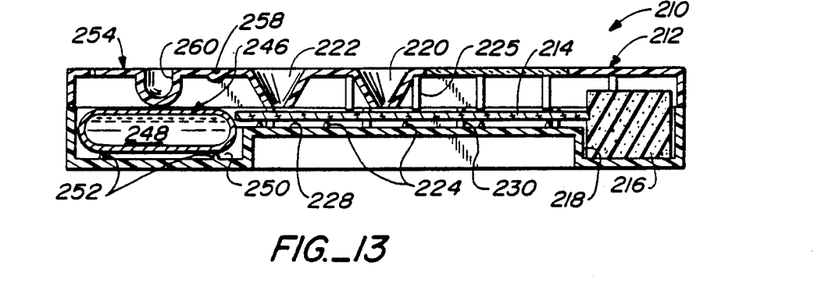
FIG. 13 is a cross-sectional view of the device of FIG. 12 taken along lines 13—13.
Figure 14:
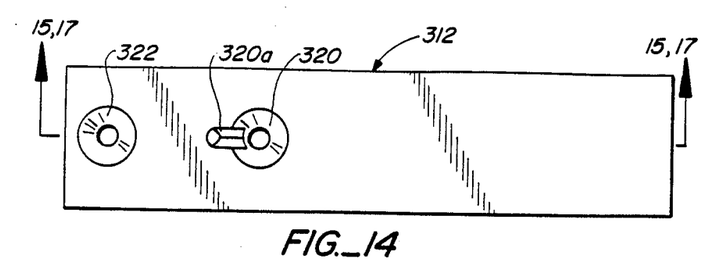
FIG. 14 is a top plan view of another embodiment of the device of the present invention.
Figure 15:
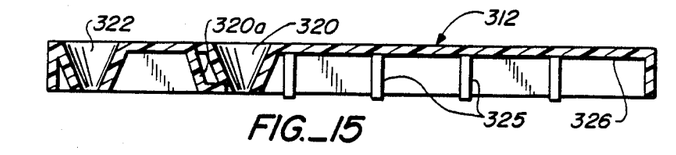
FIG. 15 is a cross-sectional view of the top half of the device of FIG. 14 taken along lines 15—15.
Figure 16:
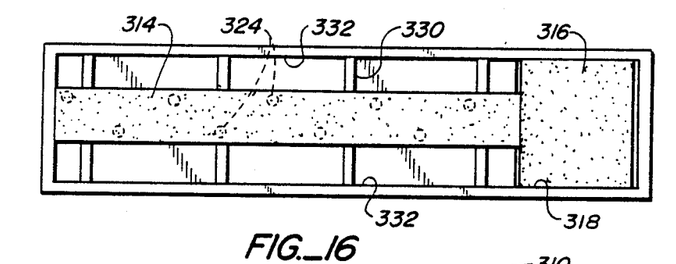
FIG. 16 is a top view of the bottom half of the device of FIG. 14.
Figure 17:
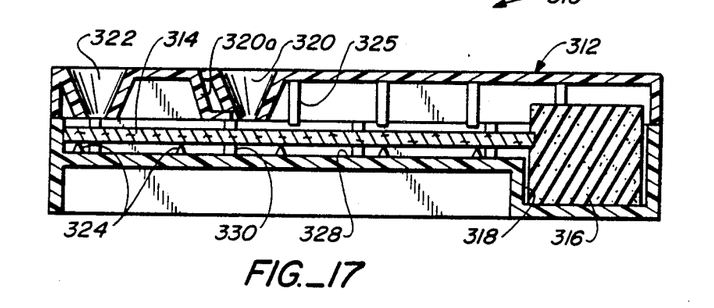
FIG. 17 is a cross-sectional view of the device FIG. 14 taken along lines 17—17.

Referring now to FIG. 1 depicts device 10. The device comprises housing 12, which can be of any suitable shape or size in accordance with the particular type of assay to be conducted. Housing 12 can be fabricated from any suitable material appropriate for the type of assay being conducted. The material used to fabricate the housing should not interfere with the sample, the sample medium, or any reagents utilized in conducting the assay including members of the single producing system. Preferably, the housing is formed from a thermoplastic material, or the like.

Device 10 further includes means in the housing for capturing a member of a specific binding pair in a zone and for allowing liquid to be transported by capillary action away from the zone. In the embodiment depicted in FIGS. 1-5 such means comprises a piece of bibulous material, a bibulous strip 14, having one or more immunosorbing zones. Preferably, the bibulous strip is non-removably confined in device 10. A liquid absorbent material 16 in liquid receiving relationship with bibulous strip 14 may optionally be included in device 10, preferably, non-removably confined in device 10. The combination of strip 14 and absorbent means 16 provides for capturing an sbp member in a zone and transporting liquid away from the zone by capillary action. Liquid absorbing member 16 is conveniently located in recess portion 18 of device 10. In the device of FIGS. 1-5 recess portion 18 is located at one end of device 10 opposite the end having first means 20 for introducing a sample and/or liquid reagent into the device. Such is by way of example only. Other embodiments will be suggested to those skilled in the art. For example, member 16 can be positioned at, near remote from means 20 for introducing the sample. Device 10 also includes second means 22 for introducing a liquid reagent and sample into the device.

The inner walls of housing 12 can contain means 24 for supportively confining strip 14 in the housing. In some circumstances it is important that the top and under side of strip 14 have limited contact with the inner walls of the housing so that the capillary action of the strip remains essentially unchanged and the strip is free to expand as it becomes wet. In other cases the underside of the strip can rest on a hydrophobic elastic pad that will assure good contact of means 20 and 22 with the top of the strip without interfering with capillary flow.

Exemplary of means 24 are protruding elements 24 found on inner walls 26 and 28 of housing 12. Elements 24 are generally integral with the inner walls of housing 12 and may be in the form of posts which are conical, oblong, oval, rectangular, triangular, or the like. A key feature of elements 24 is that they minimize the contact area with strip 14 so that the capillarity of strip 14 is not altered in any significant manner. By the term "altering in any significant manner" is meant that the capillary action of strip 14 is not altered such that the performance of the assay is significantly affected thereby reducing or eliminating the accuracy of the test. For example, sufficient capillary action must be maintained in order to be able to accurately determine the analyte in a sample.

In FIGS. 2-5, elements 24 and 25 lie in rows parallel to the longitudinal sides of housing 12. Generally, elements 24 and 25 have dimensions such as to allow slight up and down movement of the strip in the housing in the dry state and to prevent such movement when the strip is wetted by the traversing liquid. Usually, the distance of such movement is 0 mm to 3.0 mm when the strip is in the dry state. Generally, on each of the top and bottom inner walls of housing 12, there are about from 2 to 15 elements 24 or 25, respectively, per side, having a length of about 0.5 to 4 mm each. In an alternative embodiment strip 14 can be affixed to a support, thus eliminating the need for elements 24 or 25 or both. Means 30 are provided to maintain strip 14 free from contact with the inner side walls 32 of the bottom portion 34 of device 10. Such means can take the form of elements 30 protruding from walls 32. The shape of elements 24, 25, and 30 can each independently or all be rectangular, oval, triangular, oblong, conical, or the like. In general means 30 serve the same function as means 24 and 25.

Liquid absorbing member 16 is confined in recessed area 18. Member 16 can be in intimate contact with the walls of the recessed portion 18 of the housing or the walls may also contain means for supportively confining liquid absorbing member 16. In any event member 16 is confined within recess 18 of housing 12 to be maintained in liquid receiving relationship with strip 14.

Housing 12 further includes first means 20 therein for introducing the sample and/or liquid reagent into device 10. In the device pictured in FIGS. 1-5 means 20 includes an opening through which sample can be deposited on strip 14 and a liquid containment well. Such a containment well can be utilized in any configuration or shape. The well can be cylindrical, conical, rectangular, square, oval or the like or a combination thereof. The dimensions of the well can also be varied widely according to the particular assay to be conducted and the shape of the well. Generally, the well should have a volume of 10–1000 μl, preferably 50–500 μl, more preferably 100–400 μl and the walls should be sloped sufficiently to cause the liquid to flow freely to the opening at the bottom. The opening will generally be small, usually 0.3–15mm$^2$, preferably 1–10 mm$^2$ and may be square, oval, triangular, round and the like. Preferably, the opening will be designed such that it is in sufficiently good contact with strip 14 that all liquid in contact with the opening will be absorbed into the strip without leakages. Alternatively, means 20 can take the form of a septum made out of an elastomeric material such as rubber, plastic, or the like.

Housing 12 further includes second means 22 for introducing liquid reagents and the sample into device 10. Generally, the above description for first means 20 also applies to second means 22. First means 20 and second means 22 can be of the same configuration or shape or made from the same material or they may be different. Preferably the openings in means 20 and 22 will be close together, usually 1–20 mm, preferably 1–10mm, frequently 2–5 mm whereupon the wells of means 20 and 22 may be designed as a single well with a divider between the two openings.

Delivery of the sample may be made into device 10 through first means 20 or second means 22 utilizing a dropper, syringe needle, or the like containing the sample to be analyzed. Delivery of the sample into the device will result in the sample being deposited on strip 14. A liquid reagent other than sample will usually be added to the device following addition of the sample. Furthermore, additional liquid reagents may be added to the device either before or after sample addition, at least one of such reagents being added through the means not used in adding the sample. Other means for introducing the sample into the device will be suggested to those skilled in the art.

A preferred embodiment for assembly of the device of the present invention may be seen with reference to FIGS. 1–5. The present device is conveniently formed from two pieces herein referred to as top half or piece 36 and bottom half or piece 38. Pieces 36 and 38 are joined along edge lines 40 on piece 36 and 42 on piece 38. Conveniently, the two halves can include means for interlocking the halves. For example, top half 36 can contain a protrusion which is designed to snap fit with a protrusion receiving means on piece 38. After placing strip 14, and absorbent member 16, if separate from 14, into piece 38, piece 36 and piece 38 are joined together along their edges. Piece 36 and piece 38 may be sealed together to produce housing 12 by application of sonic energy, an adhesive, heat, or the like, according to conventional techniques. The preferred technique is a snap fitting. The use of top and bottom pieces for assembly of the device of the invention is merely illustrative. Other means of forming the present device, depending on the particular configuration chosen for the device, will be suggested to those skilled in the art to having reference to the disclosure contained herein.

Top half 36 of device 10 can possess an opening or transparent window to view an immunosorbing zone and may include a scale on its face to assist in quantitating the amount of analyte in the sample. For example, where quantitation is the result of measuring the length within an immunosorbing zone in which detection of signal is observed, an indicating means such as a scale adjacent to a window for observing the immunosorbing zone assists in obtaining the quantitative results.

Devices other than that depicted in FIGS. 1–5 are included as part of this invention. A number of such devices can be assembled as a single composite device that is able to assay a number of samples.

Another embodiment of a device in accordance with the present invention is depicted in FIGS. 6–9. Device 110 comprises housing 112 generally comprising bibulous strip 114 and bibulous piece 116. Top piece 136 has first means 120, second means 122 and third means 123 for introducing sample and/or liquid reagents other than the sample into the device. When sample is introduced in the third means 123, at least one of the liquid reagents will be added through means other than third means 123 following addition of the sample. In the embodiment depicted means 120, 122, and 123 are openings in piece 136.

Referring now to FIGS. 10–13 depicting device 210. The device comprises housing 212, which can be of any suitable shape or size in accordance with the particular type of assay to be conducted.

Device 210 further includes means closed in the housing for capturing a member of a specific binding pair in a zone and for allowing liquid to be transported by capillary action away from the zone. In the embodiment depicted in FIGS. 10–13 such means comprises a piece of bibulous material, a bibulous strip 214, having one or more immunosorbing zones. Preferably, the bibulous strip is non-removably confined in device 210. A liquid absorbent material 216 in liquid receiving relationship with bibulous strip 214 may optionally be included in device 210, preferably, non-removably confined in device 210. Liquid absorbing member 216 is conveniently located in recess portion 218 of device 210. In the device of FIGS. 10–13 recess portion 218 is located by way of example at one end of device 210 opposite the end having means 254 described below for breaking container 246 containing self contained liquid reagent 248.

Further enclosed, preferably, non-removably, in housing 212 is self-contained liquid reagent 248 in breakable container 246. The liquid reagent is utilized in the determination of an analyte in the sample. The liquid reagent can include members of a signal producing system such as enzyme substrates, and the like. Container 246 is located in recess 250 of device 210. Container 246 is conveniently manufactured from a breakable material such as glass, plastic, and the like. Container 246 is normally supportively confined within recess 250 by means 252 in such a manner that it is easily broken at the desired time. Means 252 is a wall or can take the form of a shoulder, rib, protrusion, or the like. Recess 250 can contain reagents for conducting an assay in dry form or diffusively bound to a support.

Housing 212 further includes means 254 for assisting in the breaking of container 246. Preferably, means 254 comprises a movable portion hinged at 258 generally lying over recessed area 250. Means 254 can be manipulated to break capsule 246. Furthermore, means 254 can also include bottom 260 lying opposite container 246. When movable portion 254 is depressed, button 260 is forced against container 246 and container 246 is broken. Members 260 can be included to assist breakage of 246.

Housing 212 further includes first means 220 and second means 222 therein for introducing a sample into device 10. In the device pictured in FIGS. 10-13 first means 220 and second means 222 are openings through which sample and liquid reagents can be deposited on strip 214 in accordance with the principle of the present invention.

Optionally, housing 212 has means 262 which will allow to immunosorbing zone or zones on the bibulous material to be visualized so that one may be able to determine the result of an assay when the immunosorbing zone is not at means 220 or means 222. Accordingly, the top portion 236 of housing 212 can be constructed entirely of a clear thermoplastic material. Alternatively, only the area allowing for visualization of the immunosorbing zone or zones can be a clear material or such area can merely be an opening in the top portion of device 210. The dimensions of the housing again depend on the particular assay being conducted.

The solvent for the sample to be analyzed and the solvent for the liquid reagents and any self-contained reagents will be an aqueous medium, which may be up to about 40 weight percent of other polar solvents, particularly oxygenated solvents of from 1 to 6, more usually of from 1 to 4 carbon atoms, including alcohols, ethers and the like. Usually, the cosolvents will be present in less than about 20 weight percent.

The pH for the medium will usually be in the range of 4-11, more usually 5-10, and preferably in the range of about 6-9. The pH is chosen to maintain a significant site of binding affinity of the binding members and optimal generation of signal by the signal producing system. Various buffers may be used to achieve the desired pH and maintain the pH during the assay. Illustrative buffers include borate, phosphate, carbonate, tris, barbital and the like. The particular buffer employed is not critical, but in individual assays, one buffer may be preferred over another.

Desirably for some assays, from about 0.05 to 0.5 weight percent of a detergent is included with the sample and/or the liquid reagents. Detergents such as sodium dodecyl sulfate (SDS), deoxycholate, CHAPS, and NP 40 find particular use for microbial and analytes and antibodies. Generally, nonionic detergents such as Triton X-100 will be useful for macromolecular analytes.

Moderate, and desirably substantially constant, temperatures are normally employed for carrying out the assay. The temperatures for the assay and production of a detectable signal will generally be in the range of about 4°-50° C., more usually in the range of about 10°-40° C., and frequently will be ambient temperatures, that is, about 15°-25° C. When the analyte is a nucleic acid, higher temperatures up to 70° C. will be useful.

When concentration in the aqueous test solution of analyte that may be assayed will generally vary from about $10^{-4}$ to about $10^{-15}$M, more usually from about $10^{-6}$ to $10^{-14}$ M. Considerations, such as the concentration of the analyte of interest and the protocol will normally determine the concentration of the other reagents.

While the concentrations of many of the various reagents in the sample and reagent solutions will generally be determined by the concentration range of interest of the analyte, the final concentration of each of the reagents will normally be determined empirically to optimize the sensitivity of the assay over the range of interest. With certain protocols, individual reagents may be used in substantial excess without detrimentally affecting the sensitivity of the assay.

Where the bibulous material is a strip, the size of strip 14 is dependent on several considerations. The primary consideration is to move unbound materials away from the immunosorbing zone, usually the area on the strip opposite first means 20 or an area between the first means 20 and absorbent material 16, and to cause binding of the sbp members to the immunosorbing zone in response to the presence of an analyte in the test solution. When liquid absorbing material 16 is not included the length and thickness of the strip control the amount of solution that can pass along the strip. If the transfer of a large volume of test solution is desired, the fluid capacity of the strip above the immunosorbing zone must be sufficient to accommodate the desired volume. If liquid absorbing material 16 is used, this volume requirement is not needed. In general, when liquid absorbent material 16 is not used, the fluid retention volume will be usually greater than 20 μL, preferably at least 50-200 μL. When liquid absorbent material 20 is used, strip retention volumes as low as 2-20 μL can be used but volumes of 20-200 μL are preferable.

Thickness of the strips is not critical and will normally be 0.1-2 mm, usually 0.15-1 mm, preferably 0.2-0.7 mm. Generally, the minimum thickness is dictated by the strength of the material and the need to produce a readily detectible signal whereas the maximum thickness will be dictated by convenience of handling and cost of the reagents.

To permit conservation of reagents and provide for samples of limited size, the width of the strip will generally be relatively narrow, usually less than 20 mm, preferably less than 10 mm. Generally, the width of the strip will not be less than about 1.0 mm and will usually range from about 2 mm to 12 mm, preferably from about 4 mm to 8 mm.

The cross-sectional dimensions of a strip have been described in the preceding discussion in terms of a rectangle for purposes of illustration and not limitation. As mentioned above, other cross-sectional shapes such as circular, triagonal, oval, etc, fall equally within the scope of this invention. The dimensions thereof can be determined by those skilled in the art with reference to the disclosure herein.

The length of the strip will depend on (1) whether an absorbent member 16 is employed, (2) the concentration of one or more of the analytes and (3) practical considerations with respect to ease of handling of device 10 and will be about 1 cm to 40 cm, usually about 2 cm to 25 cm, preferably about 4 to 20 cm but may be of any practical length. The structure of the strip can be varied widely and includes fine, medium fine, medium, medium coarse and coarse. In general, smaller pore size and finer material will provide slow capillary flow and efficient capture of bound conjugate on the strip. Courser more porous materials provide faster flow, but the efficiency of capture is reduced except where particles from the sample or a ligand reagent are involved. Selection of the porosity of the material depends on the rate of binding of the components for a given assay.

Absorbent member 16 may be comprised of the same or different bibulous material as strip 14 and can be integral with strip 14. Member 16 can be in the form of a strip, pad, cylinder, or other convenient shape. The dimensions of member 16 are dependent on some of the same factors as the dimensions for strip 14. The primary consideration is that member 16 be capable of absorbing the minimum volume of liquid required in the assay including the solvent for the sample, assay reagents, and any wash solutions as necessary.

The length of device 10 will usually be about 2–30 cm long, preferably 4–15 cm. The cross-section of the device will usually be rectangular but may be elipsoid or some other shape but will usually be flat on at least one side. The minimum and maximum cross-sectional dimensions will be 0.5 to 5 cm, preferably 1.0 to 3 cm, but may be larger when the elements of more than one device are included on a single unit. Usually, the height measured perpendicularly from the flat side will be 1–30mm, preferably 5–20 mm.

The position of means 20 and 22 and any immunosorbing zone or zones with respect to strip 14 and absorbent material 16 is governed by the basic principle of this invention and the particular assay being employed and to which the device of the present invention is adapted.

In the simplest form shown in FIGS. 1–5 the device has two openings, 20 and 22. Opening 22 is near the terminus of strip 14 and opening 20 is located between opening 22 and liquid absorbent member 16. Sample can be added through opening 20 or opening 22 followed by one or more liquid reagents which may be members of a signal producing system wherein one of the liquid reagents is added to opening 22. There reagents move along strip 14 by capillary action past the portion of strip 14 opposite opening 20. In this way un-immobilized materials such as an sbp member are carried away so that a signal can be read at opening 20. When the immunosorbing zone on strip 14 is opposite opening 20. Alternately, the sbp member can be carried to an immunosorbing zone removed from opening 20 where a signal can be read.

The minimum distance of means 20 from means 22 is usually about 1 mm. The minimum distance of an immunosorbing zone from means 20, when the immunosorbing zone is not opposite means 20, is determined by the capacity of the intervening bibulous material to non-diffusively bind an sbp member when this is required and by the flow characteristics of strip 14 that affect the efficiency of washing the immunosorbing zone. This distance will usually be one that is convenient and makes the result easy to visualize. Desirably, the immunosorbing zone, when not opposite means 20, may be at least 5 mm, preferably at least 10 mm, from the contact portion opposite means 20 in the direction of the absorbent material 16. It may be positioned any greater distance away provided the liquid reagents can pass thereto to capillary action. In this way, the immunosorbent zone is "separated" from such contact portion.

The liquid reagents, which are normally sbp members, members of the signal producing system or wash solutions if necessary, can vary widely in concentration depending upon the particular assay protocol and their role in signal production. The amounts of sbp members are selected based on the predetermined minimum detectible amounts of the analytes that are in the test solution. The amount of each of the sbp members that contacts the immunosorbing zone will preferably equal or exceed the amount of the corresponding analyte in the test solution that contacts the immunosorbing zone. However, the amount of the sbp member may be 100 or more times lower than the corresponding amount of analyte that contacts the immunosorbing zone.

One or more sbp members and members of the signal producing system may be substantially uniformly bound to an immunosorbing zone on the strip. The amount of each sbp member and member of the signal producing system bound is dependent on the particular assay protocol employed.

In carrying out an assay utilizing the present device, the protocol will normally involve combining in an aqueous medium the sample suspected of containing the analytes and other reagents as necessary for the assay protocol chosen to form the aqueous test solution. In some instances the test solution will be the sample itself. The sample may be derived from a wide variety of sources, such as physiologic fluids, illustrated by saliva, blood, serum, plasma, urine, ocular-lens, fluid, spinal fluid, etc., food products such as milk and wine, chemical processing streams, food waste water, etc.

Referring now to FIGS. 1–5, the test solution is introduced into device 10 through means 20 or 22 to contact a portion of strip 14. The test solution is drawn along strip 14 through the contact portion by capillary action. Next, a liquid assay reagent such as an enzyme labeled sbp member can be introduced into the device through means 20 or 22, usually means other than that used for the test solution. Generally, it will be preferable to add this liquid reagent to opening 22 when the test solution has been delivered to opening 20. The reagent contacts a portion of strip 14 usually including a portion of the strip contacted by the liquid reagent. Additional liquid reagents will be added depending on the requirements of the assay and may be added to either opening except that the final liquid reagent to contact the immunosorbing zone will usually be added last and frequently will be added to opening 22. This reagent can be a wash solution and may contain chemical agents forming part of the signal producing system. When an enzyme is used as a label, the chemical agents will usually include a substrate, normally in a sufficient concentration so as not to be rate limiting (greater concentration than Km), which will be appropriately buffered for the enzyme system.

As mentioned above, the contact portion can also serve as the immunosorbing zone or separate immunosorbing zones can be utilized depending on the particular assay protocol chosen. Wetting of the strip by capillary action usually is allowed to continue, so that a sufficient amount of assay reagents passes through, or becomes bound in, as the case may be, the immunosorbing zone. After the liquid has traversed the strip, the immunosorbing zone is examined for the presence of a detectible signal.

For the most part, relatively short times are involved for the solutions to traverse the strip. Usually, the traverse of the solutions over the strip will take at least 30 sec and not more than 1 hour, more usually from about 1 min to 30 min. When an enzyme is used in the signal producing means, the development of the signal will generally range from 30 sec. to 5 min.

A sufficient time is allowed to elapse prior to measuring the signal to produce an amount of the signal producing compound. Once opportunity has been given for production of a detectable signal, it is known whether or not at least one of the analytes in the sample is present at or above a predetermined minimum detectible amount.

The strip may be untreated prior to the assay or can be coated with a wide variety of materials to provide for enhanced properties. Coatings may include protein coatings, polysaccharide coatings, synthetic polymers, sugars or the like, which are used particularly to enhance the stability of any materials bound to the strip. These compounds can also be used to control nonspecific binding of materials, such as antibodies, antigens, labels and binding or the like.

The strip can be activated with reactive functionalities to provide for covalent bonding of the organic materials to be conjugated to the strip such as those described in U.S. Pat. No. 4,168,146, the relevant disclosure of which is incorporated herein by reference.

Sbp members and, where desired, members of the signal producing system, can be bound to the piece of bibulous material or strip by adsorption, rather than covalent bonding. Such binding can be non-diffusive or diffusive depending on whether or not the assay protocol requires movement of such member along the strip. This can involve contacting the bibulous material with a solution containing the materials to be bound to the strip and allowing the strip to dry or, when binding is diffusive, application of the dry solvent. When the binding is non-diffusive, subsequent treatment with proteins, detergents, polysaccharides, or other materials capable of blocking non-specific binding sites may be required.

In other embodiments of the device of the present invention, a third opening is located between the first two openings (FIGS. 6-9) or a liquid reagent is contained in a breakable sealed container within the device (FIGS. 10-13). After addition of the sample through one of the openings, the final liquid reagent to contact the immunosorbing zone can be added by breaking the sealed container or by addition to the same or a different opening. This reagent can be added to any opening in accordance with the principle of the present invention, provided only that both the sample and the liquid reagent contact the immunosorbing zone, but it will frequently be desirable to add this reagent at an opening that is not between the opening to which sample was added and the immunosorbing zone. During or prior to the period of flow of this reagent, additional reagents can be added provided only that they be entrained by the flow and carried to the immunosorbing zone. The flow will also provide that the locations on the strip opposite the first opening and the detection zone will be washed with minimum operational steps.

One application of the device provides for timed reagent additions even though the operator carries out all the steps in rapid succession. In this protocol, sample and necessary reagents are added through one opening, secondary reagents are added through a second opening, and the final liquid reagent to contact the immunosorbing zone is added through a third opening located furthest upstream and relative to the general direction of flow (FIGS. 6-9) or is provided by breaking a container in the device (FIGS. 10-13). Since time will be required for capillary migration of this reagent past each of the openings, the time of incubation at each opening prior to transport to that opening of reagents added at a different opening or by breaking the container can be controlled by the distances between each of the openings and the breakable container.

Another embodiment of this invention concerns the shape of the wells within the openings. While these will frequently be cylindrical, conical, oval or rectangular as mentioned above, it will be desirable in some cases to provide an adjacent depression or shelf, e.g., 320a, connected or within one or more wells, where a reagent or sample can be deposited without contacting the strip (FIG. 14-17). Addition of a second reagent will cause the first reagent to mix with it and the mixture will flow onto the strip.

The device of the invention can be utilized in a wide variety of assay methods and protocols. The following examples are provided by way of illustration and not limitation. U.S. Pat. No. 4,366,241, which is incorporated herein by reference, describes an assay method for the determination of sbp members. The device has an immunosorbing zone to which an sbp member is fixed against diffusive movement. The immunosorbing zone generally lies opposite to the entry for the sample solution. In liquid-receiving relationship, with the immunosorbing zone is a liquid absorbing zone.

Usually employed in the method in conjunction with the device is a signal producing system which includes a label conjugated to an sbp member which can be bound diffusively to the bibulous support or provided as a liquid reagent. The immunosorbing zone may include one or more additional members of the signal producing system which are bound to the zone in a manner to permit or inhibit diffusive movement of a signal producing system component. The liquid reagent in the breakable container will usually contain any remaining members of the signal producing system in a wash buffer. In accordance with the method protocol, the amount of label bound in the immunosorbing zone is related to the amount of analyte in the sample.

The signal producing system provides for a detectible signal in the immunosorbing zone in relation to the amount of label bound thereon which can be compared to a signal level based on a standard having a known amount of analyte or based on a comparison with portion of the bibulous material other than the immunosorbing zone.

One specific embodiment of the method of U.S. Pat. No. 4,366,241 is described in U.S. Pat. No. 4,632,901. The latter patent discloses an apparatus and process for conducting immunoassays. The apparatus comprises a first member which is a membrane or a filter to which is bound an antibody, typically a monoclonal antibody. Such membrane with antibody corresponds to an immunosorbing zone. The method further employs a second member which is composed of absorbent material which acts when in contact with the first member of induce flow through the first member when a fluid sample is added to it. This method can be conducted with the device of the present invention by applying a sample containing an antigenic analyte through a first opening to the first member which an antibody is non-diffusively bound. Addition of the sample is followed by addition of a liquid medium containing enzyme labeled antibody against the antigen being assayed through a second opening. The first member is then contacted with enzyme substrates and washed by addition of a solution of substrate to the first opening or to a third opening or by means of breaking a breakable container. The presence of enzyme labeled antibody on the first member as indicated by the formation of enzyme catalyzed product after washing is indicative of the presence of the antigen in the sample being assayed. The device and protocol of the present invention is an improvement over the protocol of U.S. Pat. No. 4,632,901 in that all separate washing steps have been eliminated and only one or two liquid reagents are required that are not incorporated in the device.

Another example of an assay method in which the present device can be utilized is described in U.S. Patent Application Ser. No. 701,464, filed Feb. 14, 1985. The method is for determining the presence of an analyte in a sample suspected of containing the analyte. The method involves contacting a test solution containing the sample and a first sbp member with a portion of a strip of bibulous material capable of being traversed by the test solution through capillary action. The first sbp member is capable of binding the analyte. The strip contains a second sbp member integral therewith for concentrating and non-diffusively binding the first sbp member at a small situs or immunosorbing zone on the strip separated from the contact portion of the strip. A detectible signal is produced in relation to the presence of the analyte in the test solution. The test solution passes through the immunosorbing zone as the test solution traverses the bibulous material. After the test solution has been allowed to traverse at least a portion of the strip, the strip is contacted with a developer solution containing members of a signal producing system. Using the device of the present invention such developer solution can be introduced through the second opening in the device or by breaking the breakable container. If necessary, the strip can be contacted with any other members of the signal producing system either prior to or after contacting with the developer solution by introduction through one of the openings. The detectible signal produced at the immunosorbing zone is then compared with the signal detectible at a portion of the strip other than the immunosorbing zone or to the signal produced by a control sample to determine the analyte in the sample. The signal produced at the immunosorbing zone can have a sharp-edged distinctive pattern that provides a sharp contrast to the signal produced at adjacent sites on the strip when analyte is present in the test solution.

A further example of an assay method in which the present device can be employed is described in U.S. Patent Application Ser. No. 904,595, filed Sept. 5, 1986. Such a method is directed to determining the presence of an analyte in a sample suspected of containing the analyte. The method involves contacting a test solution containing the sample, an antibody for the analyte, and a conjugate of the analyte and a label with a contact portion of a piece of bibulous material capable of being traversed in at least one direction by the test solution through capillary action. The bibulous material contains an immunosorbing zone having a first receptor capable of binding to the conjugate non-diffusively bound on the bibulous material separate from the contact portion. The bibulous material further contains a second receptor capable of binding the antibody to the analyte between the immunosorbing zone and the contact portion. The second receptor is non-diffusively bound to the bibulous material. At least a portion of the test solution is allowed to traverse the bibulous material by capillary action and thereby contact the immunosorbing zone. The zone is examined for the presence of the conjugate. To this end, the strip can be exposed to a signal producing means capable of interacting with the label, usually an enzyme substrate, to produce a signal in relation to the amount of analyte in the test solution. Preferably, the immunosorbing zone is washed prior to or during exposure to the signal producing means. The signal producing means can be introduced into a device of the present invention through the second opening located between the second receptor and the immunosorbing zone. The zone is thereby washed and the signal produced at the immunosorbing zone can then detected.

Another example of an assay in which the present device can be employed is disclosed in U.S. Patent Application Ser. No. 928,233, filed Nov. 7, 1986. In the method the presence of more than a predetermined minimum detectible amount of one or more analytes in a sample suspected of containing a plurality of analytes is determined. Each analyte is an sbp member. The method comprises contacting with a test solution containing the sample and predetermined amount of two or more first sbp members, each respectively analogous to one of the analytes, a contact portion of a piece of bibulous material capable of being traversed in at least one direction by the test solution by capillary migration. The bibulous material contains predetermined amounts of two or more second sbp members, each respectively capable of binding one of the analytes and corresponding first sbp member. The second sbp members are non-diffusively bound to the bibulous material at least between the contact portion and a predetermined site or immunosorbing zone on the piece of bibulous material separated from the contact portion such that in the presence of more than a predetermined amount of an analyte the analogous first sbp member migrates at least to the predetermined site on the piece of bibulous material. Next, at least a portion of the test solution is allowed to traverse the bibulous material by means of capillary migration. The predetermined site is examined for the presence of one or more of the first sbp members, which is usually indicated by the presence of a detectible signal. The predetermined site can be exposed to a signal producing means capable of interacting with the first sbp members to produce a detectible signal at the predetermined site in relation to the presence of one or more of the analytes in the sample. Such signal producing means can be introduced through the second opening or by breaking a breakable container into the device of the invention to contact the bibulous material.

Another example of an assay technique in which the present device finds use is described in U.S. Patent Application Ser. No. 928,771, filed Nov. 7, 1986. In this method the presence of an analyte in a sample suspected of containing the analyte is determined. The analyte is an sbp member. The method comprises contacting, with a test solution containing the sample and a first sbp member analogous to the analyte, a contact portion of a piece of bibulous material capable of being traversed in at least one direction by the test solution by capillary migration. The bibulous material contains a second sbp member capable of binding the analyte and the first sbp member. The second sbp member is non-diffusively bound to the bibulous material at least at a portion thereof between the contact portion and a small situs or immunosorbing zone on the piece separated from the contact portion. The surface area of the situs is substantially less than that of the piece of bibulous material. The situs is capable of binding the first sbp member not bound to said second sbp member. Next, at least a portion of the test solution is allowed to traverse the bibulous material by means of capillary migration and thereby contact the situs. The situs is examined for the presence of the first sbp member at the situs, which is usually indicated by the presence of a detectible signal.

Such signal can be generated by exposing the situs to a signal producing means capable of interacting with the first sbp member to produce a detectible signal at the situs in relation to the amount of analyte in the sample. The signal producing means can be introduced into the device of the invention by means of a second opening or by breaking a breakable container. The signal at the situs is distinguishable from signal detectible at portions of the bibulous material other than the situs.

Still another example of an assay method in which the present device can be employed is described in U.S. Pat. No. 4,552,839 and a variant thereof in U.S. Pat. No. 4,623,461. U.S. Pat. No. 4,552,839 discloses methods and compositions for determining the presence of analytes in a particle containing medium, where the analyte of interest may be bound or unbound to a particle in a sample. By contacting the assay medium with a bibulous material at a liquid air interface, a small situs, usually a thin band or concentrated point, of particles can be obtained adjacent the interface, which site provides a signal which can be related to the presence of analyte in the sample. The particles include synthetic particles, cells, and immune complex aggregates. The size and nature of the particles, as well as the nature of the aqueous medium, can be used to modulate the formation of the small site. In some embodiments of this method one or more members of a signal producing system in a liquid medium are next contacted with the bibulous material. Such liquid medium can be introduced through the second opening into a device in accordance with the present invention.

In one specific embodiment of the present invention the device can be used for serological testing as, for example, the testing for antibodies to, for example, HIV, HBV, rubella, syphilis, etc. In such an embodiment, the sample is combined with an antigen in a liquid medium. Any immune complex formed must be separated from nonspecific immunoglobulin in the sample. Only then can anti-immune globulin be allowed to contact the immune complex. Where the label is an enzyme, the immune complex must be separated from labeled anti-immunoglobulin before contacting it with an enzyme substrate. By using the device of FIGS. 10–13, these steps can be accomplished by adding all the reagents in succession. A serum sample is combined with latex beads coated with antigen and added to opening 222 of device 210. Alternatively, the shelf 320a of device of FIG. 14–17 is incorporated at opening 222 of device 210 (FIGS. 10–13). The serum sample is delivered to the shelf and a suspension of the latex bead is added to opening 222, thereby flushing the serum and the latex suspension onto the strip. Enzyme labeled receptor immunoglobulin is next added to opening 220 and the breakable container is broken thus releasing a wash solution containing enzyme substrates. As the substrate solution migrates toward the wells, the immunoglobulin receptor solution has time to migrate toward and contact the latex beads that have become entrapped opposite opening 222 where it can react with any bound antibodies. The substrate solution subsequently migrates past the latex beads in the opposite direction thereby effectively washing the beads and exposing them to substrate which is converted to detectable product in proportion to the amount of conjugate that has bound to the beads. The operator can return to view the presence or absence of color at opening 222 after a period at least long enough to permit these events to occur. In this method, opening 220 can also serve as a color reference to assist in defining the amount of color at the opening 222.

A related method can be used to assay for chlamydia antigen. For example, by using a device with a breakable capsule containing developer (FIGS. 10–13) the sample and antibody to chlamydia can be added sequentially through one opening, a solution containing enzyme labeled anti-immunoglobulins can be added through a second opening and the capsule can be broken to release enzyme substrate and wash solution. During an incubation period, the sample will absorb into the strip and antigen-antibody complex will be bound to the strip if antigen is present. The enzyme labeled anti-immunoglobulin will than contact the complex by capillary migration or by migration driven by the capillary flow of the enzyme substrate and wash solution and will bind to any complex that is present. The wash solution will than wash the complex free of excess conjugate, and finally provide the substrate to permit enzyme catalyzed formation of a detectable product at the first opening.

A device with two openings and a detection zone can be used in an assay for human chorionic gonadotrophin (HCG). In this method, a conjugate of an enzyme with anti-HCG is dried on the strip at the first opening and a second anti-HCG antibody is immobilized at a detection zone on the strip downstream from the first opening. The assay can be conducted by adding a sample suspected of containing HCG at the first opening and simultaneously adding a developer solution containing enzyme substrate at the second opening. During subsequent incubation, HCG binds to the conjugate, the complex is carried by the moving developer to the detection zone where it binds, and the bound complex acts on the substrate to produce color at the detection zone when HCG is present in the sample. As a matter of convenience, the present device can be provided in a kit in packaged combination with reagents in predetermined amounts for use in assaying for an analyte. Depending on the particular assay involved, the reagents can include enzyme labeled sbp member, substrate for the enzyme, buffers, any additional substrates and cofactors required by the enzymes, dye precursors, and the like. In addition, other additives may be included, such as stabilizers, buffers, and the like. The relative amounts of the various reagents may be varied widely, to provide for concentrations in solution of the reagents which substantially optimize the sensitivity of the assay. Where appropriate, the device of the present invention can be packaged in an air-tight package in order to maintain the activity of any immunochemical agents.

The patents and patent applications referred to in the above description are each incorporated herein by reference in their entirety.

Although the foregoing invention has been described in some detail by way of illustration and example for the purposes of clarity and understanding, it will be obvious that certain changes or modifications may be practiced within the scope of the appended claims.

What is claimed is:

1. A device for conducting an assay, said device comprising:
   (a) a housing,
   (b) means enclosed in said housing for capturing a first member of a specific binding pair (sbp) in a zone and for allowing liquid to be transported by capillary action away from said zone, (c) first inlet means in said housing for introducing a sample into the device, and
(d) second inlet means in said housing for introducing liquid reagent other than said sample into the device without also introducing said liquid reagent through said first inlet means.
a portion of said means for capturing being in liquid receiving relationship with said first inlet means and said second inlet means.

2. The device of claim 1 wherein the means for capturing comprises a bibulous material that is immunosorbing or is capable of being rendered immunosorbing.

3. The device of claim 2 wherein said bibulous material has a member of a specific binding pair (sbp) bound thereto.

4. The device of claim 3 wherein said sbp member is an antibody or an antigen.

5. The device of claim 2 wherein a second piece of bibulous material is in liquid receiving relationship with said bibulous material.

6. The device of claim 5 wherein said bibulous material is composed of glass fibers.

7. The device of claim 1 which further includes one or more reagents confined for subsequent release in at least one container enclosed in said housing for conducting an assay method for the determination of an analyte in a sample.

8. The device of claim 7 wherein said reagent or reagents are contained in a water insoluble breakable container.

9. The device of claim 8 wherein said reagent or reagents are in an aqueous medium.

10. The device of claim 9 wherein said medium comprises a member of a signal producing system capable of generating a signal in relation to the amount of an analyte in the sample.

11. The device in claim 7 wherein said reagent or reagents are in an aqueous wash solution.

12. The device of claim 2 wherein said bibulous material has in contact with it a dry, water dispersible, sbp member conjugated to a label.

13. The device of claim 12 wherein said label is selected from the group consisting of catalysts, enzymes, chromogens, radioactive substances, and dispersible particles.

14. The device of claim 1 wherein said first inlet means is an opening in said device.

15. The device of claim 14 wherein said opening is adjacent to said zone.

16. The device of claim 1 wherein said second inlet means is an opening in said device.

17. The device of claim 1 wherein said first inlet means is proximate said second inlet means.

18. The device of claim 1 wherein said means for capturing is a bibulous material capable of entrapping beads coated with an sbp member.

19. The device of claim 1 wherein said means for capturing includes a second sbp member-non-diffusively bound to said zone.

20. The device of claim 7 which further comprises means integral with said housing for releasing said liquid reagent from said container.

21. The device for claim 1 which further includes means for viewing at least a portion of said zone.

22. The device of claim 21 wherein said first inlet means lies between said second inlet means and said viewing means.

23. A device for conducting an assay, which device comprises:
a housing,
a first opening in said housing for introducing a sample suspected of containing an analyte into said device,
bibulous material enclosed in said housing, said bibulous material being capable of transporting liquid away from the point of introduction of said sample, and
a second opening in said housing for introducing liquid reagent other than said sample into said device without contacting said bibulous material at said point of introduction with said liquid reagent except by capillary transport,
a portion of said bibulous material being in liquid receiving relationship with said first opening and said second opening.

24. The device of claim 23 wherein the bibulous member has on its surface a member of a specific binding pair (sbp)

25. The method of claim 24 wherein said sbp member is non-diffusively bound to said bibulous member.

26. The device of claim 24 wherein said sbp member is an antigen or antibody.

27. The device of claim 24 wherein said bibulous material is a strip and said sbp member is bound to a portion thereof.

28. The device of claim 23 which further includes a liquid reagent for conducting an assay confined in a breakable container, and means integral and said housing allowing for breaking said container.

29. The device of claim 28 wherein said liquid reagent contains an enzyme substrate.

30. The device of claim 25 wherein said bibulous material has in contact with it a dry water soluble sbp member conjugated to a label.

31. The device of claim 30 wherein said label is selected from the group consisting of catalysts, chromogens, radioactive substances, and dispersible particles.

32. The device of claim 23 which further includes a second bibulous material in liquid receiving relationship with said bibulous material.

33. The device of claim 32 wherein said bibulous material and said second bibulous material are bound together to provide a single unit.

34. The device of claim 23 wherein said bibulous material is a strip with a portion having a pore size different from the remainder of said strip.

35. The device of claim 23 which further includes a window in said housing for viewing at least a portion of said bibulous material.

36. The device of claim 35 wherein said first opening lies between said second opening and said window.

37. The device of claim 23 wherein said second opening is proximate said first opening.

38. The device of claim 23 wherein said liquid reagent is an aqueous medium.

39. The kit for conducting an assay method, said kit comprising in a packaged combination with other assay components the device of claim 23.

40. A device for conducting an immunoassay for an analyte in a sample suspected of containing said analyte, which device comprises:
a housing having means for viewing the interior thereof, first inlet means for introducing a sample therein, and second inlet means for introducing therein an aqueous solution other than said sample, and a piece of bibulous material enclosed in said housing, said bibulous material having a specific binding pair (sbp) member non-diffusively bound to a situs on said bibulous material, said bibulous material further having a labeled sbp member diffusively deposited on said bibulous material between said means for viewing and said second inlet means.

a portion of said bibulous material being in liquid receiving relationship with said first inlet means and said second inlet means and said situs being in viewing relationship with said means for viewing.

41. The device of claim 40 which further includes a breakable container enclosed in a portion of said housing, said container having confined therein an aqueous medium.

42. The device of claim 40 which further comprises absorbent material enclosed in said housing in liquid receiving relationship with said bibulous material.

43. The device of claim 40 wherein said analyte is a protein and said labeled sbp member is an antibody.

44. In a device for conducting an assay, said device comprising inlet means for introducing a sample containing an analyte into said device and means for transporting liquid away from said inlet means, the improvement which comprises second inlet means other than said inlet means for introducing liquid reagent other than said sample into said device and means for transporting said liquid reagent by capillaRy action away from said second inlet means, a portion of said means for transporting being in liquid receiving relationship with said inlet means and said second inlet means.

45. The device of claim 44 wherein said inlet means and said other means are openings in said device.

46. The device of claim 44 wherein said liquid reagent is an aqueous medium.

47. The device of claim 44 wherein said transporting means is a bibulous material.

48. A method for conducting an immunoassay for an analyte suspected of being in a sample, which method comprises:

(a) introducing a test solution comprising a sample suspected of containing an analyte into the device of claim 1 through said first inlet means to allow said test solution to traverse at least a portion of said zone.

(b) introducing a liquid agent into said device through said second inlet means whereby said agent traverses at least a portion of said zone, and (c) observing said zone for the presence of a signal in relation to the presence of analyte in said sample.

49. In a method for conducting an assay for an analyte in a sample suspected of containing said analyte, which method comprises:

introducing a test solution comprising said sample onto a bibulous material in an assay device through inlet means and allowing said test solution to traverse at least a portion of said bibulous material contained in said device, introducing into said device immediately thereafter a liquid agent to traverse at least a portion of said bibulous material, and observing said bibulous material for the presence of a signal in relation to the presence of analyte in said sample, the improvement which comprises introducing said liquid agent into said device at a second inlet means such that said liquid agent does not also enter said device through said first inlet means.

50. A method for detecting an antibody in a sample suspected of containing said antibody, which method comprises:

introducing beads of less than about $5\mu$ diameter coated with antigen complementary with said antibody and said sample into a first opening of the device of claim 28, introducing an enzyme labeled receptor for immunoglobulin into a second opening of said device breaking the breakable container of said device to release a liquid reagent containing a substrate or substrate precursor for said enzyme, incubating for a time sufficient for product to form on the strip of said device opposite said first opening when enzyme is present at said opening, and comparing the amount of product formed opposite said first opening with the product formed at said second opening or with the product formed with a sample free of said antibody.

51. A method for detecting an antigen in a sample suspected of containing said antigen, which method comprises:

introducing beads of less than about $5\mu$ diameter coated with antibody complementary with said antigen and said sample into a first opening of the device of claim 28, introducing an enzyme labeled receptor for said antigen into a second opening of said device breaking the breakable container of said device to release a liquid reagent containing a substrate or substrate precursor for said enzyme, incubating for a time sufficient for product to form on the strip of said device opposite said first opening when enzyme is present at said opening, and comparing the amount of product formed opposite said first opening with the product formed at said second opening or with the product formed with a sample free of said antigen.

52. The method of claim 51 wherein said antigen is a microbial antigen.

* * * * *